(12) United States Patent
Steller et al.

(10) Patent No.: US 9,212,167 B2
(45) Date of Patent: Dec. 15, 2015

(54) MITOCHONDRIAL TARGETED STIMULATORS OF APOPTOSIS

(75) Inventors: Hermann Steller, New York, NY (US); Cristinel Sandu, New York, NY (US); Anshuman Kelkar, New York, NY (US); Nidhi Gangadhar, New York, NY (US)

(73) Assignee: The Rockefeller University, New York, NY (US)

( * ) Notice: Subject to any disclaimer, the term of this patent is extended or adjusted under 35 U.S.C. 154(b) by 49 days.

(21) Appl. No.: 13/611,128

(22) Filed: Sep. 12, 2012

(65) Prior Publication Data

US 2013/0244325 A1 Sep. 19, 2013

Related U.S. Application Data

(60) Provisional application No. 61/533,288, filed on Sep. 12, 2011.

(51) Int. Cl.
*A01N 55/02* (2006.01)
*A61K 31/555* (2006.01)
*C07D 401/14* (2006.01)
*C07D 303/46* (2006.01)
*C07D 303/40* (2006.01)
*C07D 413/14* (2006.01)
*C07D 405/14* (2006.01)

(52) U.S. Cl.
CPC ............ *C07D 401/14* (2013.01); *C07D 303/40* (2013.01); *C07D 303/46* (2013.01); *C07D 405/14* (2013.01); *C07D 413/14* (2013.01)

(58) Field of Classification Search
None
See application file for complete search history.

(56) References Cited

U.S. PATENT DOCUMENTS

| 2005/0197403 A1 | 9/2005 | Harran et al. | |
| 2008/0199439 A1* | 8/2008 | McLendon | 424/93.7 |

OTHER PUBLICATIONS

Straub, "Targeting IAPs as an Approach to Anti-Cancer Therapy", Curr.Top.Med.Chem., Feb. 2011, vol. 11, No. 3, pp. 291-316.*
Sandu et al. "*Drosophila* IAP antagonists form multimeric complexes to promote cell death." J. Cell. Biol., vol. 190, No. 6, pp. 1039-1052 (2010).
Stevenson et al. "A novel approach for the synthesis of the peripheral benzodiazepine receptor ligand PK111905." Tet. Left., vol. 48, pp. 7137-7139 (2007).
Sun et al. "Structure-based design, synthesis, evaluation and crystallographic studies of conformationally constrained Smac mimetics as inhibitors of the x-linked inhibitor of apoptosis protein (XIAP)." J. Med. Chem., vol. 51(22), pp. 7169-7180 (2008).
Bertrand et al. "cIAP1 and cIAP2 facilitate cancer cell survival by functioning as E3 ligases that promote RIP1 ubiquitination." Molecular Cell, vol. 30, pp. 689-700 (2008).
Li et al. "A small molecule Smac mimic potentiates TRAIL- and TNF-mediated cell death." Science, vol. 305, pp. 1471-1474 (2004).
Glover et al. "A high-throughput screen for identification of molecular mimics of Smac/DIABLO utilizing a fluorescence polarization assay." Analytic Biochemistry, vol. 320, pp. 157-169 (2003).
Mannhold et al. "IAP antagonists: promising candidates for cancer therapy." Drug Discovery Today, vol. 15, No. 5/6, pp. 210-219 (2010).

* cited by examiner

*Primary Examiner* — Jeffrey S. Lundgren
*Assistant Examiner* — Stephanie Springer
(74) *Attorney, Agent, or Firm* — Heslin, Rothenberg, Farley & Mesiti P.C.

(57) ABSTRACT

Pro-apoptotic compounds having a tripartite structure:

A-L-B are disclosed. In these compounds A is an IBM mimetic moiety; L is a linker and B is a moiety that binds to a protein on the outer mitochondrial membrane. The compounds are useful for inducing cell apoptosis and therefore treating cancer. An example of such a compound is

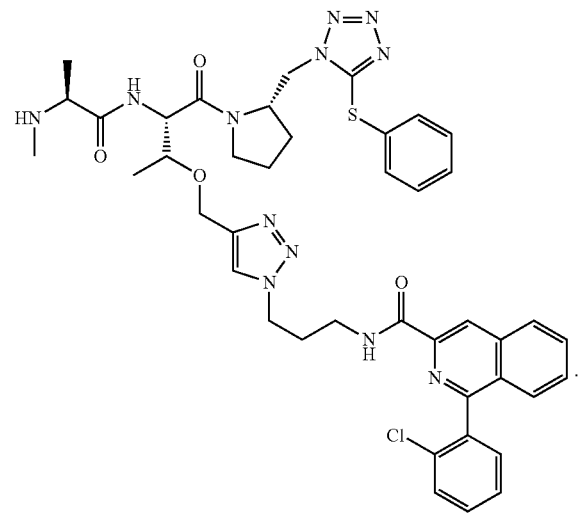

4 Claims, 2 Drawing Sheets

MITOCHONDRIAL TARGETED STIMULATORS OF APOPTOSIS

CROSS-REFERENCE TO RELATED APPLICATIONS

This application claims priority to U.S. Provisional Patent Application No. 61/533,288, filed Sep. 12, 2011, which is hereby incorporated herein by reference in its entirety.

FEDERALLY SPONSORED RESEARCH

The following invention was made with Government support under contract number 5RO1 GM060124-12 awarded by NIH. The Government has certain rights in this invention.

FIELD OF THE INVENTION

The invention relates to compounds that bind to and inhibit Inhibitor of Apoptosis (IAP) Proteins on the mitochondrial outer membrane. Therefore, these compounds are useful to induce apoptosis in cells and to inhibit the growth of tumors.

BACKGROUND OF THE INVENTION

Inhibitor of Apoptosis (IAP) proteins are commonly over-expressed in human tumors and thereby contribute to tumor cell survival. As a result, IAPs have become attractive drug targets in cancer therapy. Several small molecules targeting IAPs are in clinical trials. The design of these compounds is based on a short IAP-binding motif (IBM) that is present in natural IAP-antagonists, such as *Drosophila* Reaper/Hid/Grim and mammalian Smac. Derivatives of the Hid IBM have proven most effective. They are reviewed in Vaux, D. L. (2009). *Biology Reports* 1:79, the contents of which are incorporated herein by reference. Although these IBM-mimetics show some promise, they have some serious limitations. In particular, all available compounds primarily target cIAP1/2, but are poor inhibitors of XIAP. Improved targeting of XIAP would be desirable, since this protein is a potent cell death inhibitor that is over-expressed in human tumors. It has been shown that inactivation of XIAP protects against tumorigenesis in the mouse, and that loss of the XIAP-antagonist ARTS causes increased malignancies [Schile et al., (2008) *Genes Dev.* 22, 2256-2266; Garcia-Fernandez et al., (2010) *Genes Dev.* 24, 2282-2293]. We now disclose that using a "generic" mitochondrial targeting sequence to direct a short IBM-peptide to the mitochondrial outer membrane is sufficient for potent inhibition of XIAP and selective killing of human cancer cell lines.

SUMMARY OF THE INVENTION

In one aspect, the invention relates to a pro-apoptotic compound having a tripartite structure:

A-L-B wherein
A is an IBM mimetic moiety;
L is a linker and
B is moiety that binds to a protein on the outer mitochondrial membrane.

In another aspect, the invention relates to methods for inducing cell apoptosis comprising exposing the cell to a compound described herein.

In another aspect, the invention relates to methods for inhibiting tumor growth comprising exposing a tumor to a compound described herein.

In another aspect, the invention relates to compounds of formula wherein Q is —O— or —NH—. The compounds are useful as intermediates in the synthesis of compounds of formula A-L-B, in which the linker L incorporates a triazole.

DETAILED DESCRIPTION OF THE INVENTION

In its most basic aspects, the invention relates to compounds, methods of using the compounds and intermediates for making compounds having the structure:

A-L-B wherein
A is an IBM mimetic moiety;
L is a linker and
B is residue that binds to a protein on the outer mitochondrial membrane.
In a particular embodiment, L is a linker of formula wherein Y is chosen from ($C_1$-$C_{20}$)hydrocarbon, ($C_1$-$C_{20}$) oxaalkyl and 1,2,3-triazole; and m and n are chosen independently from zero and integers from 1 to 10. In such embodiments, the compounds have the formula

In a subset of these, Y is 1,2,3-triazole and the compounds have the formula wherein one of the residues A-$CH_2$—$(CH_2)_n$— and B—$CH_2$—$(CH_2)_m$— is attached to the triazole ring at the ring nitrogen shown with unsatisfied valence and the other of the residues A-$CH_2$—$(CH_2)_n$— and B—$CH_2$—$(CH_2)_m$— is attached to the triazole ring at one of the two ring carbons.

Peripheral Benzodiazepine Receptor (PBR) is a transmembrane multimeric protein complex primarily located in the outer mitochondrial membrane of the cells. It is composed of an isoquinoline carboxamide-binding protein, voltage-dependent anion channel and adenine nucleotide translocase. Because of the location of PBR, compounds that target (specifically bind to) PBR provide one library from which "B" can be drawn. Other proteins that are localized on the outer membrane of mitochondria can also be targeted. Examples include palmitoyl transferase (CPT1), monoamine oxidase (MAO), voltage-dependent anion channel (VDAC), and b-cell lymphoma 2 (Bcl-2) proteins.

Head Involution Defective protein (HID) is a proapoptotic protein from *Drosophila* that is also localized on the outer mitochondrial membrane. It induces cell death by antagonizing *Drosophila* Inhibitor of Apoptosis Protein 1. All IAP proteins have one or three tandem baculovirus IAP repeat (BIR) domains of 70-80 amino acids with a conserved core sequence $C\phi_2C\phi_6W\phi_3D\phi_5H\phi_6C$ (wherein $\phi$ is any amino acid). The BIR domain folds into three-stranded $\beta$ sheets surrounded by four $\alpha$ helices, and a zinc ion, coordinated by the three cysteines and one histidine, lies in the hydrophobic core. BIR domains have been shown to be important in the anti-apoptotic activity of IAPs. They mediate the interactions with different cytosolic target proteins such as activated caspase 3, 7, and 9 and natural IAP protein antagonists such as Smac/Diablo and HtrA2/Omi.

To maintain homeostasis, several endogenous proteins operate as antagonists of IAPs. Some examples are Smac/Diablo, HtrA2/Omi, ARTS and XAF1. These antagonist proteins are sequestered in organelles to prevent an interaction with cytosolic IAPs. Under apoptotic stimulus are they released into the cytosol to bind to IAPs. Their apoptotic activity is mediated by the IAP binding motif (IBM), which is exposed after proteolytic cleavage (except for XAF1) at the N terminus of the protein. IAP activity is deregulated in almost all human cancers due to the overexpression of IAP proteins or the inhibition of their endogenous antagonists.

HID uses a conserved N-terminal IAP Binding Motif (IBM) and binds to BIR1 and BIR2 domains of DIAP1, thereby blocking its anti-apoptotic function in caspase neutralization. BIR domains and IBM proteins are evolutionarily conserved through humans, and the BIR-IBM interaction is known in structural detail for *Drosophila* and human proteins. Small molecule mimics of the IBM peptides are known in the art. These molecules, also termed "Smac-mimetics", bind BIR domains of human IAPs with nanomolar affinity in vitro and trigger IAPs degradation in cancer cells. The synthesis of two such molecules (Compound 1PA and Compound 2PA) (shown below) was described by Harran et al. in US published application 2005-0197403.

1PA

-continued

2PA

They bind specifically human XIAP and *Drosophila* DIAP1 and trigger cell death of human cancer cells.

IBM mimetics of the art have focused on BIR domain binding; no attempt has been made to target them to the mitochondrial membrane. The compounds disclosed herein have been designed to localize to the mitochondrial outer membrane, with the expectation that this will increase apoptotic activity or selectivity or both in cancer cells.

The instant compounds are designed to bridge a small molecule IBM-mimetic through a linker to a small molecule drug that has previously been shown to bind specifically a protein that resides on the outer mitochondrial membrane.

Since the three-dimensional structure of BIR3 binding pocket is known, a person of skill will be aware not to attach the moieties derived from the known IBM-mimetics (the "A" residues) to "L" at a position that will interfere with binding. For example, in attaching the linker L to the IBM-mimetic 1PA, the attachment is made through the phenyl of the benzyl ether. An appropriate intermediate for carrying out this process is obtained by modifying the benzyl ether component of the O-benzylthreonine in the published synthesis:

-continued

In the modified synthesis, R' can be bromine, iodine or a protected phenolic hydroxyl, depending on the nature of the linker to be appended.

Similarly, in attaching the linker L to the HID-mimetic 2PA, the attachment can be made at the site of the propargyl ether. When the linker L is to incorporate triazole as Y, the ALB compound can be made directly from 2PA via 1,3-dipolar cycloaddition or Cu(I) catalyzed cycloaddition using well-known "CLICK" chemistry [see Huisgen R., Centenary Lecture-1,3-Dipolar Cycloadditions. *Proceedings of the Chemical Society of London,* 1961; Kolb et al. *Angewandte Chemie International Edition,* 40(11): 2004-2021 (2001).; and Luo et al. J. *Org. Chem.* 71: 9244-9247 (2006)]:

-continued

The reaction shown above uses the propargyl ether that already exists in 2PA. When it is desired that "m" in the linker be other than zero, the appropriate ω-bromoalkyne can be substituted for propargyl bromide in the published synthesis of 2PA analogs.

When it is desired that the linker L incorporate hydrocarbon or oxaalkylene chains as Y, the ALB compound can be made by replacing the propargyl alcohol in 2PA with a silyl ether protecting group on t-Boc threonine followed by deprotection of the silylether and reaction with the appropriate alkyl bromide, oxaalkylbromide, alkanol tosylate or oxaalkanol tosylate:

Mitochondrial-targeting molecules that are the basis for the residue "B" ideally would not induce apoptosis by themselves. Two examples of mitochondrial-targeting small molecules are (R)-etomoxir and PK-11195. (R)-Etomoxir (compound 50PA below) was designed as an anti-diabetic drug, and it specifically binds to carnitine palmitoyl transferase on the outer mitochondrial membrane.

A second mitochondrial-targeting molecule is PK-11195, which targets the peripheral benzodiazepine receptor (PBR).

PK-11195

(R)-Etomoxir and PK11195 are commercially available and their syntheses are described in the literature. When "click" chemistry is used, the following intermediates may be used to synthesize A-L-B's containing etomoxir and PK-11195:

wherein Q is —O— or —NH—.

Additional small molecule ligands for the PBR are well known in the literature and include: DAA-1097, DAA-1106, emapunil, FGIN-127, FGIN-143 and SSR-180575.

Additional compounds that can be used as mitochondrial targeting sequences (moiety B) are the following: (1) Bcl2 inhibitors such as ABT-737, chelerythrine chloride, gossypol, apogossypolone, ABT-263, HA14-1, antimycin A, TW-37 and obatoclax, which are disclosed in Vogler et al. *Cell Differentiation and Death* 16, 360-367 (2009), incorporated herein by reference; (2) monoamine oxidase inhibitors such as benmoxin, hydralazine, iproclozide, iproniazid, isocarboxazid, mebanazine, nialamide, octamoxin, phenelzine, pheniprazine, phenoxypropazine, pivalylbenzhydrazine, procarbazine, safrazine, caroxazone, echinopsidine, furazolidone, linezolid, zyvoxam, tranylcypromine, brofaromine, metralindole, minaprine, moclobemide, pirlindole, toloxatone, lazabemide, pargyline, rasagiline, selegiline, metfendrazine, amiflamine, bazinaprine, befloxatone, befol, cimoxatone, clorgyline, esuprone, methylene blue, sercloremine, tetrindole, thesputiaint, tyrima, D-deprenyl, ladostigil, milacemide and mofegiline); and (3) VDAC inhibitors such as oblimersen (G3139) and cyclosporine A.

In compounds of formula A-L-B, B may be chosen from wherein
R$^1$ and R$^2$ are independently chosen from H and CH$_3$;
R$^{10}$ is (C$_1$-C$_{10}$)alkyl;
p is chosen from zero and integers from 1 to 10; and
X is hydrogen or halogen.

Examples of A-L-B include:

Throughout this specification the terms and substituents retain their definitions.

Alkyl is intended to include linear, branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

Alkoxy or alkoxyl refers to groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues (including cycloalkyls) in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups.

Hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include, but are not limited to, e.g., benzyl, phenyl, phenethyl, cyclohexylmethyl and naphthylethyl.

The term "halogen" means fluorine, chlorine, bromine or iodine. In one embodiment, halogen may be fluorine or chlorine.

As used herein, and as would be understood by the person of skill in the art, the recitation of "a compound"—unless expressly further limited—is intended to include salts of that compound. Thus, for example, the recitation "a compound of formula as depicted above, would include salts in which the nitrogen of the N-terminal N-methylalanine is protonated and is paired with any counterion. In a particular embodiment, the term "compound" refers to the compound or a pharmaceutically acceptable salt thereof. The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, nitrogen, sulfur, phosphorous, fluorine, and chlorine include $^2H$, $^3H$, $^{13}C$, $^{14}C$, $^{15}N$, $^{35}S$, $^{32}P$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. For example, compounds having the present structures except for the replacement of hydrogen by deuterium or tritium, or the replacement of a carbon by a $^{13}C$- or $^{14}C$-enriched carbon are useful as analytical tools or probes in biological assays.

The term "moiety" when used to describe A or B, refers to a known ligand for HID or IBM or a ligand for a protein on the surface of the mitochondrial outer membrane (such as the peripheral benzodiazepine receptor), respectively, minus an atom, a $C_1$ to $C_3$ substituent or a hydroxy functional group that has become part of the bond to L:

For example, an "IBM-mimetic moiety" is a known IBM or HID ligand such as 2PA minus the propargyl of the ester:

so that it may attach to the linker:

Similarly, a "moiety that binds to a protein on the outer mitochondrial membrane" is a known ligand for a protein on the surface of an outer mitochondrial membrane such as etomoxir:

50PA minus the ethyl of the ester:

so that it may attach to the linker:

The combination of these two exemplars provides

A specific example with a triazole-containing linker is:

wherein A is an IBM mimetic moiety; L is a linker and B is a moiety that binds to a protein on the outer mitochondrial membrane.

While it may be possible for the compounds described herein to be administered to patients as the raw chemical, it is often desirable to present them as a pharmaceutical composition. According to a further aspect, the present invention provides a pharmaceutical composition comprising a compound together with one or more pharmaceutical carriers and optionally one or more other therapeutic ingredients. The carrier(s) must be "acceptable" in the sense of being compatible with the other ingredients of the formulation and not deleterious to the recipient thereof.

The formulations for administration to patients include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

The synthesis of a representative compound of the invention, in which "A" is derived from 2PA, "B" is derived from an analog of PK11195 and the linker "L" is a triazole is shown in Scheme 1 and described in detail below.

Scheme 1

(1)

(11)

(12)

(S)-Boc-2-[5-(Toluene-4-sulfonyl)-tetrazol-1-ylmethyl]-pyrrolidine (1): (S)-2-(azidomethyl)-1-Boc-pyrrolidine (480 mg, 2.1 mmol) was added to a flask containing p-toluenesulfonyl cyanide (420 mg, 2.3 mmol) and a stir bar (no solvent). The flask was placed in a 80° C. bath and reaction proceeded for 48 hours. The reaction was concentrated in vacuo. The crude amber oil was purified by flash silica gel chromatography using a hexane/ethyl acetate gradient. The product (780 mg, 91% yield) was obtained as a colorless oil. $^1$H-NMR (500 MHz, CDCl$_3$): δ 8.01 (broad d, J=18 Hz, 2H), 7.44 (m, 3H), 4.85-4.70 (m, 2H), 4.52-4.48 (m, 1H), 3.50-3.34 (m, 2H), 2.49 (s, 3H), 2.01-1.71 (m, 4H), 1.40 & 1.33 (2 s, 9H). ESI-MS (m/z) for C$_{18}$H$_{25}$N$_5$O$_4$S (exact mass 407.16): [M+H]$^+$ calc. 408.2, obs. 408.2; [M+Na]$^+$ calc. 430.2, obs. 430.2.

(S)-Boc-2-(5-Phenylsulfanyl-tetrazol-1'-ylmethyl)-pyrrolidine (2): Sulfone 1 (780 mg, 1.91 mmol), 12 ml anhydrous acetonitrile, thiophenol (882 mg, 8 mmol), and K$_2$CO$_3$ (830 mg, 6 mmol) were mixed in a round bottom flask with a stir bar. The reaction was stirred for 48 hours at ambient temperature. The mixture was then filtered through a pad of Celite and the filtrate was concentrated in vacuo. The crude material was purified by flash silica gel chromatography using a hexane/ethyl acetate gradient. The product (670 mg, 97% yield) was obtained as a colorless oil. ESI-MS (m/z) for C$_{17}$H$_{23}$N$_5$O$_2$S (exact mass 361.16): [M+H]$^+$ calc. 362.2, obs. 362.2.

Compound 3: Sulfide 2 (200 mg, 0.55 mmol) was treated with TFA (2 mL) for 5 minutes at room temperature. The reaction was concentrated in vacuo, which resulted in a clear oil. ESI-MS (m/z) for C$_{12}$H$_{15}$N$_5$S (exact mass 261.16):

[M+H]+ calc. 262.2, obs. 262.2. The crude material was used as is in the next step without further purification.

Compound 4: Under an argon atmosphere, in a round bottomed flask equipped with a stir bar, Boc-Thr-OH (2 g, 9 mmol) was dissolved in 10 mL of anhydrous DMF. The resulting solution was cooled down to 4° C. (ice-water bath) before a separately premixed suspension of NaH (0.65 g, 27 mmol) in 5 mL DMF was slowly introduced while stirring. After 30 minutes, the flask was warmed to room temperature. An 80% by weight solution of propargyl bromide in toluene (2 ml, 18 mmol) was added to the reaction. After one hour, the reaction was concentrated in vacuo. The residual brown oil was diluted in ether and washed with 0.1 M HCl (3 times), then water (3 times). The ether layer was dried with sodium sulfate, filtered, and concentrated in vacuo. The crude oil was purified by flash silica gel chromatography using a hexane, 2% acetic acid/ethyl acetate, 2% acetic acid gradient. A tan oil was obtained (2 g, 87%). $[\alpha]_D$=+17.8 (c=0.5, MeOH). $^1$H-NMR (600 MHz, CDCl$_3$): δ 5.26 (d, J=9.1 Hz, 1H), 4.33 (m, 2H), 4.16 (m, 2H), 2.44 (t, J=2.3 Hz, 1H), 1.46 (s, 9H), 1.26 (d, J=6.2 Hz, 3H). ESI-MS (m/z) for $C_{12}H_{19}N_6O_5$ (exact mass 257.13): [M+H]+ calc. 258.1, obs. 258.2.

Compound 5: Sulfide 3 (0.55 mmol) and acid 4 (157 mg, 0.61 mmol) were added to a flask containing anhydrous DMF (10 mL). Diisopropylethylamine (312 ul, 237 mg, 1.83 mmol) and 2-(7-aza-1H-benzotriazole-1-yl)-1,1,3,3-tetramethyluronium hexafluorophosphate (HATU) (302 mg, 0.8 mmol) were added. After 1 hour, the reaction was concentrated in vacuo. The oil was diluted in ethyl acetate and washed with water (3 times). The organic layer was, dried over sodium sulfate, filtered over celite, and evaporated. The resulting oil was purified by flash silica gel chromatography using a linear hexane to ethyl acetate gradient. The desired material was isolated as a white solid (220 mg, 80%). $^1$H-NMR (600 MHz, CDCl$_3$): δ 7.60 (m, 2H), 7.40 (m, 3H), 5.52 (d, J=8.4 Hz), 4.70 (dd, J=4.2, 13.7 Hz, 1H), 4.55 (pentuplet, J=3.9 Hz, 2H), 4.50 (dd, J=3.8, 8.9 Hz, 1H), 4.36 (dd, J=8.1, 13.7 Hz, 1H), 4.23 (m, 2H), 4.04 (m, 1H), 3.67 (m, 2H), 2.42 (t, J=2.3 Hz, 1H), 1.92-1.82 (m, 4H), 1.44 (s, 9H), 1.24 (d, J=6.3 Hz, 3H). ESI-MS (m/z) for $C_{24}H_{32}N_6O_4S$ (exact mass 500.22): [M+H]+ calc. 501.2, obs. 501.2.

Compound 6: Thiotetrazole 5 (220 mg, 0.44 mmol) was treated with neat TFA (2 mL) for 5 minutes at room temperature. The reaction was concentrated in vacuo, resulting in a clear oil. ESI-MS (m/z) for $C_{19}H_{24}N_6O_2S$ (exact mass 400.17): [M+H]+ calc. 401.2, obs. 401.2. The crude material thus obtained was used in the next step without further purification.

Compound 7: Amine 6 (0.44 mmol) and Boc-(Me)Ala-OH (168 mg, 0.66 mmol) were added to a flask with DMF (5 mL). To this flask diisopropylethylamine (171 mg, 1.32 mmol, 230 uL) and HATU (200 mg, 0.53 mmol) were added. After 1 hour, the reaction was concentrated in vacuo. The oil was diluted in ethyl acetate and washed with water 3x. The organic layer was evaporated and the resulting oil was purified by flash silica gel chromatography using a hexane/ethyl acetate gradient. A white solid was obtained (230 mg, 90%). $^1$H-NMR (500 MHz, CDCl$_3$): δ 7.60 (m, 2H), 7.40 (m, 3H), 4.73 (m, 2H), 4.66 (dd, J=4.2, 13.7 Hz, 1H), 4.55 (m, 1H), 4.38 (dd, J=7.7, 13.7 Hz, 1H), 4.22 (m, 2H), 4.05 (p, J=5.6 Hz, 1H), 3.74 (m, 1H), 3.66 (m, 1H), 2.81 (s, 3H), 2.43 (s, 1H), 1.92-1.80 (m, 4H), 1.50 (s, 9H), 1.34 (d, J=4.9 Hz, 3H), 1.21 (d, J=6.3 Hz, 3H). ESI-MS (m/z) for $C_{28}H_{39}N_7O_5S$ (exact mass 585.27): [M+H]+ calc. 586.3, obs. 586.2.

Compound 8: 3-Chloropropylamine HCl (6.5 g, 0.05 mol) and sodium azide (10 g, 0.15 mol) were dissolved in 50 mL water. The reaction proceeded at 80° C. for 48 hours. 10 N NaOH (6 mL) was then added, and the product was extracted with ether and concentrated in vacuo. Bulb to bulb distillation (Bp=65-75° C. at 20-22 torr) afforded a clear oil (4 g, 80%). $^1$H-NMR (500 MHz, CDCl$_3$): δ 3.38 (t, J=6.7 Hz, 2H), 2.81 (t, J=6.8 Hz, 2H), 1.73 (p, J=6.8 Hz, 2H).

Compound 9: PK 1195 (25 mg, 0.071 mmol) and 6 N HCl (1 mL) was added to a thick walled glass pressure flask. The flask was then sealed and heated at 110° C. for 24 hours. The reaction was concentrated in vacuo, dissolved in a solution of water/acetonitrile (1:1), frozen and lyophilized. A white powder was obtained (19 mg, 97%). $^1$H-NMR (500 MHz, CDCl$_3$): 8.46 (s, 1H), 8.11 (d, J=8.2 Hz, 1H), 7.85 (t, J=7.4 Hz, 1H), 7.41-7.68 (m, 6H). ESI-MS (m/z) for $C_{16}H_{10}ClNO_2$ (exact mass 283.04): [M+H]+ calc. 284.0, obs. 284.2.

Compound 10: Under argon, carboxylic acid 9 (19 mg, 0.067 mmol) and amine 8 (35 mg, 0.35 mmol) were mixed in anhydrous DMF (1 mL), diisopropylethylamine (37 μA, 27 mg, 0.21 mmol). HATU (51 mg, 0.134 mmol) was dissolved separately in anhydrous DMF (0.5 mL) and then introduced via syringe to the reaction. After 30 minutes, the reaction was concentrated in vacuo. The oil was diluted in methylene chloride and washed with 0.1 M HCl (3x) then water (2x). The methylene chloride layer was dried over sodium sulfate, filtered, and concentrated in vacuo. A colorless solid was obtained (24 mg, 99%). ESI-MS (m/z) for $C_{19}H_{16}ClN_5O$ (exact mass 365.01): [M+H]+ calc. 366.1, obs. 366.2.

Compound 11: Azide 10 (24 mg, 0.066 mmol) and alkyne 7 (47 mg, 0.08 mmol) were mixed in ethanol:water (1:1, v:v, 2 ml). $CuSO_4$ (82.5 mg, 0.33 mmol) was dissolved in water (0.5 ml) and added to the reaction followed by sodium ascorbate (264 mg, 1.32 mmol) in water (0.5 ml). The reaction flask was immersed in a 35° C. bath for 30 minutes. The reaction was concentrated in vacuo and extracted with methylene chloride. The combined methylene chloride layers were washed with water (3x). The crude product was concentrated in vacuo. A green powder was obtained (70 mg). ESI-MS (m/z) for $C_{47}H_{55}ClN_{12}O_6S$ (exact mass 950.38): [M+H]+ calc. 951.4, obs. 951.3.

Compound 12: Carbamate 11 was treated with a solution of TFA and 1,2-ethanedithiol (5 mL+0.5 mL) for 10 minutes. The product was concentrated in vacuo then precipitated with cold ether. The crude material was purified by flash silica gel chromatography using an ethyl acetate:methylene chloride:triethylamine (4.5:4.5:1) to methylene chloride:methanol:triethylamine (7:2:1) gradient. The desired material was obtained as TFA salt; white powder (58 mg, 91% yield for two steps). $^1$H-NMR (500 MHz, CDCl$_3$): δ 8.64 (s, 1H), 8.40 (m, 1H), 8.07 (d, J=8.2 Hz, 1H), 7.94 (d, J=7.8 Hz, 1H), 7.85 (s, 1H), 7.78 (t, J=7.4 Hz, 1H), 7.70 (d, J=8.4 Hz, 1H), 7.61 (m, 4H), 7.51 (m, 3H), 7.37 (m, 3H), 4.75 (m, 2H), 4.66 (d, J=12.3 Hz, 1H), 4.56 (m, 1H), 4.45 (m, 3H), 3.62 (q, J=7.3 Hz, 3H), 3.54 (q, J=6.4 Hz, 2H), 2.41 (s, 3H), 2.25 (p, J=6.6 Hz, 2H), 1.47 (t, J=7.2 Hz, 2H), 1.30 (d, J=7.1, 3H), 1.25 (d, J=5.9 Hz, 3H). $^{13}$C-NMR: 165.4, 157.6, 144.8, 137.7, 136.6, 133.4, 133.1, 131.4, 131.0, 130.2, 129.9, 129.8, 129.7, 129.1, 128.6, 128.4, 127.4, 126.9, 123.4, 120.4, 60.0, 56.2, 54.7, 52.9, 48.3, 47.8, 47.7, 36.4, 34.9, 30.8, 27.3, 24.1, 19.2, 16.4, 8.1. ESI-MS (m/z) for $C_{42}H_{47}N_{12}O_4S$ (exact mass 850.33): [M+H]+ calc. 851.3, obs. 851.4.

In similar fashion Compound 15 was prepared from compound (7) using compound (13), the triethylene glycol analog of (8), in place of (8):

(15)

Compound 13: Under argon, carboxylic acid 9 (14 mg, 0.05 mmol) and 11-azido-3,6,9-trioxaundecan-1-amine (16 mg, 0.075 mmol) were mixed in anhydrous DMF (1 mL) in the presence of diisopropylethylamine (44 ul, 32 mg, 0.25 mmol). HATU (23 mg, 0.06 mmol) was dissolved separately in anhydrous DMF (1 mL) and then introduced via syringe to the reaction. After 30 minutes, the reaction was concentrated in vacuo. The oil was diluted in methylene chloride and washed with 0.1 M HCl (3×) then water (2×). The methylene chloride layer was concentrated in vacuo. The resulting oil was diluted in water/acetonitrile (1:1), frozen and lyophilized. A colorless solid was obtained (23 mg, 96%). ESI-MS (m/z) for $C_{24}H_{26}ClN_5O_4$ (exact mass 483.17): [M+H]$^+$ calc. 484.17, obs. 484.3.

Compound 14: Azide 13 (23 mg, 0.04 mmol) and alkyne 7 (35 mg, 0.06 mmol) were mixed in ethanol:water (1:1, v:v, 2 ml). An aqueous solution of $CuSO_4$ (65.2 mg, 0.25 mmol) in 0.5 ml of water was then added to the reaction followed by sodium ascorbate (200 mg, 1 mmol) in water (0.5 ml). The resulting solution was immersed in a water bath at 35° C. for 30 minutes. The reaction was concentrated to dryness under high vacuum and the residue was taken in methylene chloride and washed with water (3×). The crude product was concentrated in vacuo. A light green solid was obtained (50 mg). ESI-MS (m/z) for $C_{52}H_{65}ClN_{12}O_9S$ (exact mass 1068.44): [M+H]$^+$ calc. 1069.5, obs. 1069.2. This was used as is in the next step.

Compound 15: Carbamate 14 (20 mg, 0.019 mmol) was treated with neat TFA (1 mL) for 10 minutes. The product was concentrated under reduced pressure and the crude product was precipitated with cold ether. The solid was purified by reverse phase HPLC (C18, 19×150 mm, 130 Å, 5 μm) using the linear gradient 5% acetonitrile in water (0.05% TFA) to 95% acetonitrile in water (0.05% TFA) in 30 minutes. The desired material was obtained as a TFA salt; clear oil (18 mg, 85% yield). $^1$H-NMR (500 MHz, CDCl$_3$): δ 8.65 (m, 2H), 8.33 (m, 1H), 8.09 (d, J=8.2 Hz, 1H), 7.86 (s, 1H), 7.79 (m, 1H), 7.68 (m, 1H), 7.63 (m, 1H), 7.57 (m, 2H), 7.50 (m, 1H), 7.46 (m, 2H), 7.40 (m, 3H), 4.74 (broad multiplet containing water, 14H), 4.12 (m, 1H), 4.0 (m, 1H), 3.80-3.52 (m, 8H), 2.74 (s, 3H), 1.98 (m, 2H), 1.75 (m, 1H), 1.67 (m, 1H), 1.58 (d, J=6.8 Hz, 3H), 1.28 (d, J=5.9 Hz, 3H). ESI-MS (m/z) for $C_{47}H_{57}ClN_{12}O_7S$ (exact mass 968.39): [M+H]$^+$ calc. 969.5, obs. 969.4.

Figure 1:
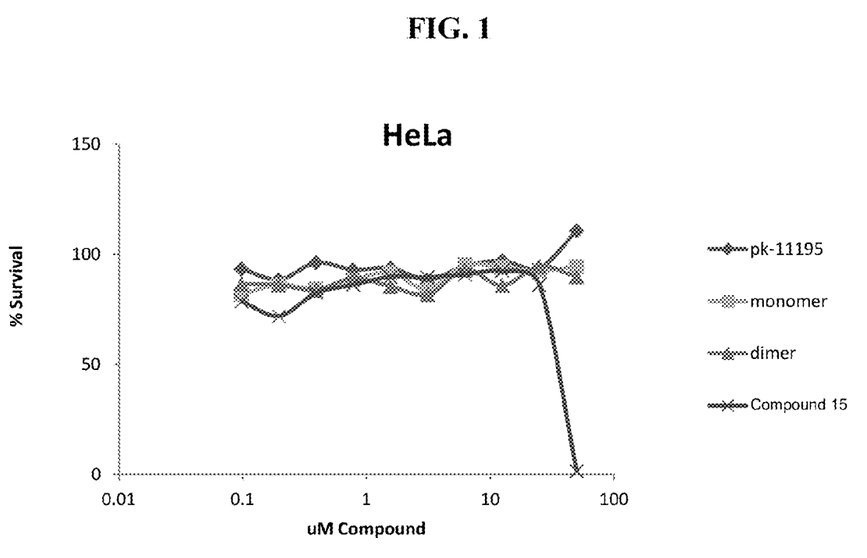
FIG. 1 is a graph illustrating percent survival of HeLa cells as a function of concentration in µM of four test compounds. Three are not compounds of the invention; the fourth is a compound of the invention.

In addition to 1PA and 2PA, other HID-mimetics or Smac-mimetics include, for example, compounds 1-26 in FIG. 1 of Mannhold et al. *Drug Discovery Today* 15 (5/6), 210-219 (2010); compound AEG40730 in Bertrand et al. *Mol. Cell* 30, 689-700 (2008); compounds 20, 21 and 25 in Sun et al. *J. Med. Chem* 51, 7169-7180 (2008), all of which are incorporated herein by reference. These and other HID-mimetics can be attached to L as described above.

Figure 2:
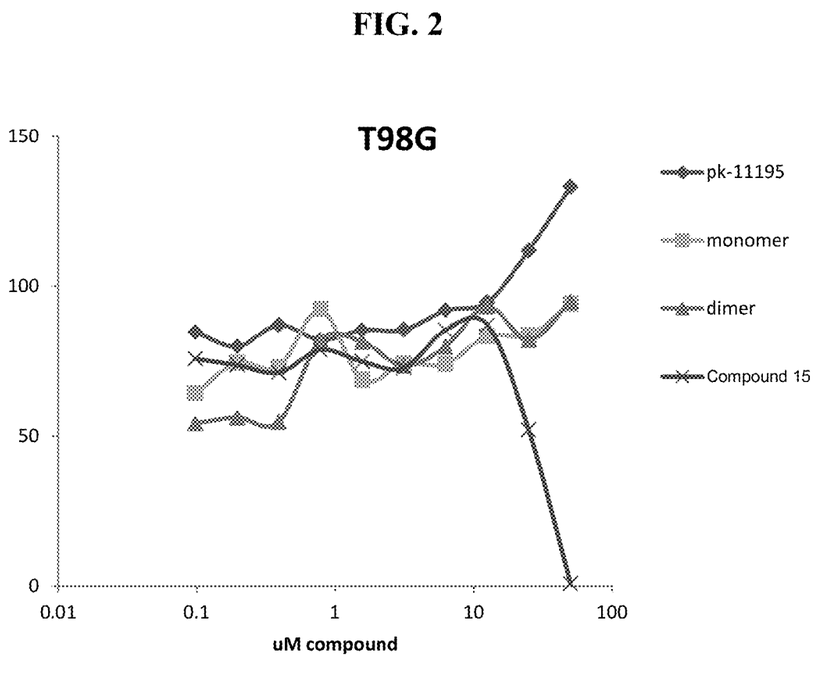
FIG. 2 is a graph illustrating percent survival of T98G cells as a function of concentration in µM of four test compounds. Three are not compounds of the invention; the fourth is a compound of the invention.

The compound described above as Compound 15 was tested for its effect on the viability of cells using Alamar Blue staining. This reagent takes advantage of the conversion by healthy cells of a non-fluorescent molecule, resazurin, to the brightly red-fluorescent resorufin. The assay was performed in 384 well plate format, and the fluorescence (560 nm Ex/590 nm Em) was detected and quantified using a Perkin-Elmer Envision plate reader. Four samples were compared. Samples were the compound identified as 2PA in paragraph [0014] (i.e. just "A" without "L" or "B"), a dimer of 2PA (i.e. A-L-A, wherein L is $C_6H_4$):

PK11195 alone and Compound 15. Ten-point dose responses were performed in both HeLa and T98G cells to determine the concentration at which each compound was effective. In FIGS. 1 and 2 it is shown that, while the monomer, dimer, and PK11195 alone do not kill at any concentration (up to 50 μM) in either cell line, Compound 15 kills both HeLa and T98G cells effectively at 50 μM.

To verify the induction of apoptosis by Compound 15, HeLa cells were treated with 40 μM of the compound and incubated for 3 or 6 hours in the presence and absence of pan-caspase inhibitor ZVAD-FMK. Apoptotic cells were counted at the indicated times in each condition. Quantification of apoptotic cells showed that Compound 15 can induce cell death, and the caspase inhibitor can prevent this induction of cell death.

The invention claimed is:
1. A compound of formula:

wherein
L is a linker of formula

Y is chosen from $(C_1-C_{20})$hydrocarbon, linear or branched $(C_1-C_{20})$oxaalkyl and 1,2,3-triazole;
m and n are chosen independently from zero and integers from 1 to 10; and
$R^1$ and $R^2$ are independently chosen from H and $CH_3$.

2. A compound according to claim 1 wherein L is chosen from wherein q is an integer from 1 to 5 and t is an integer from 3 to 10.

3. A compound of formula

4. A compound of formula

* * * * *